United States Patent [19]

Kricka

[11] Patent Number: 5,512,451
[45] Date of Patent: Apr. 30, 1996

[54] ENHANCEMENT OF CHEMILUMINESCENT REACTIONS

[75] Inventor: Larry J. Kricka, Berwyn, Pa.

[73] Assignee: British Technology Group Limited, London, England

[21] Appl. No.: 217,845

[22] Filed: Mar. 25, 1994

Related U.S. Application Data

[63] Continuation-in-part of Ser. No. 41,233, Apr. 1, 1993, abandoned.

[30] Foreign Application Priority Data

Apr. 1, 1993 [GB] United Kingdom ............... 9306888

[51] Int. Cl.$^6$ ............... C12Q 1/28; C07H 15/00
[52] U.S. Cl. ............... 435/28; 435/7.9; 435/7.91; 435/968; 536/17.1; 540/541; 544/69; 548/110
[58] Field of Search ............... 435/28, 7.9, 7.91, 435/810, 968, 975; 436/546, 808; 536/17.1; 540/541; 544/69; 548/110

[56] References Cited

U.S. PATENT DOCUMENTS 5,242,842 9/1993 Sundrehagen ............... 436/536

OTHER PUBLICATIONS

Anspach F., High Performance Liquid Affinity . . . Anal Biochem 179:1 May 15, 1989, pp. 171–181.

Primary Examiner—Ralph J. Gitomer
Attorney, Agent, or Firm—Nixon & Vanderhye

[57] ABSTRACT

In enhanced chemiluminescent (ECL) reactions of a fused aromatic diacyl cyclic hydrazide such as luminol, a peroxidase enzyme catalyst, an oxidant such as hydrogen peroxide and an enhancer, it has been found advantageous to use a combination of an organoboron enhancer such as 4-biphenylboronic acid with a non boron-containing enhancer, especially a phenolic or aromatic amine enhancer, particularly 4-iodophenol. ECL reactions are useful in diagnostic assay.

30 Claims, 1 Drawing Sheet

ENHANCEMENT OF CHEMILUMINESCENT REACTIONS

This application is a continuation-in-part of application Ser. No. 08/041,233, filed Apr. 1, 1993, now abandoned.

BACKGROUND OF THE INVENTION

1. Field of the Invention

The present invention relates to an enhanced chemiluminescent reaction especially for use in a diagnostic assay and to a diagnostic Kit for use in the assay.

2. Description of the Related Art

A chemiluminescent reaction is a chemical reaction which results in the emission of light. The luminescent emission is generally of sufficient duration to enable the light emitted to be detected or measured, and thereby to allow the detection or quantification of an analyte. The chemiluminescent reaction with which this invention is concerned is that between a fused aromatic diacyl cyclic hydrazide (FADCH), especially a 2,3-dihydro-1,4-phthalazinedione (DPD), most especially luminol, with an oxidant, especially hydrogen peroxide, and a peroxidase enzyme, especially horseradish peroxidase, which catalyses the oxidation of the FADCH by the oxidant. The oxidation is accompanied by emission of light.

Luminescent assays making use of the above-mentioned reaction include several types. This invention is concerned primarily with those in which the presence or amount of peroxidase is determined. It includes predominantly assays wherein the peroxidase is conjugated to a ligand in order to label it and a luminescent reaction is used to detect or quantitate the label. This category includes ELISAs, competitive EIAs and nucleic acid hybridization assays, based on peroxidase labels. However, assays for measurement of free peroxidase, e.g. for analytical purposes, are also included.

A review of luminescent assays has been published by L. J. Kricka, Clinical Chemistry 37, 1472–1481 (1991).

The sensitivity of the peroxidase-catalysed chemiluminescent oxidation of FADCHs can be enhanced by including in the reagents an enhancer, for example a 6-hydroxybenzothiazole (European Patent No. 87959 B or U.S. Pat. No. 4,842,997), a phenol selected from a narrowly defined class (European Patent No. 116454 B or U.S. Pat. No. 4,598,044), or an aromatic amine selected from a narrowly defined class (U.K. Patent No. 2162946 B or U.S. Pat. No. 4,729,950). A further class of substituted phenols that enhance chemiluminescent reactions of this type are phenols substituted in ortho and/or para positions by imidazolyl or benzimidazolyl (U.K. Patent No. 2205945 B or U.S. Pat. No. 5,043,266). These patents are owned by British Technology Group Ltd. European Patent Application Publication No. 219352 A (Minnesota Mining and Mfg. Co.) describes various aromatic amines, including some of those previously cited in U.K. Patent No. 2162946 A, as enhancers. Other patent applications describing different enhancers include European Patent Applications 384,271 A (Takeda), 361,470 A (Fujirebio), 455,471 A (Hitachi Chemical) and 505,198 A (Sanyo) and U.S. Pat. No. 5,279,940 (Kissel, assignor to Eastman Kodak). Recently, the present inventor has found a novel range of chemiluminescent enhancers that comprise a group of organoboron compounds. These are described in UK Patent Application No. 2265459 A or PCT Application WO 93/16195 which were unpublished at the priority date of the present application. It is an object of the invention to extend the range of effective enhancers. This is a difficult task because no theory or mechanism has been published to explain how one should attempt to select candidate compounds to try as enhancers. For the purposes of the present application the term "enhancer" and related terms will be used to mean compounds that increase the total light output or the signal:background ratio of a chemiluminescent assay, at at least one concentration of compound.

SUMMARY OF THE INVENTION

It has been found that the light output (signal) and/or signal:background ratio of light output from a chemiluminescent reaction of a fused aromatic diacyl cyclic hydrazide (FADCH), a peroxidase enzyme catalyst and an oxidant, may be increased, and/or the background light output decreased, by performing this reaction in the presence of a combination of enhancers one of which is an organoboron enhancer and the other of which is an organic enhancer not containing a boron atom, preferably a phenolic enhancer. "Signal" means the level of light output in the presence of the peroxidase, "background" in its absence.

Many of the combinations of enhancers have been found to increase the signal and/or signal:background ratio to a level higher than the predicted additive effect of using the individual enhancers in combination.

The invention includes firstly a method of increasing the light output of the chemiluminescent reaction, secondly a method of assay carried out using that reaction, and thirdly a kit of separate components for use in the assay, the kit comprising the combination of enhancers, preferably together with the FADCH or the peroxidase or both, and optionally also the oxidant.

DESCRIPTION OF THE PREFERRED EMBODIMENTS

The combination of enhancers may affect the signal, background and/or signal/background ratio in a number of ways. The signal may be increased (i) to a level greater than that of the higher of the individual enhancers when used at that concentration, but less than their predicted additive value, or (ii) to a level greater than the predicted additive value of the combined enhancers at that concentration. The former effect (i) is hereinafter referred to as a Type I effect and the latter (ii) as a Type II effect, the best example of synergistic enhancement.

The signal:background ratio may similarly be increased (i) to a level greater than the higher of the individual enhancers but less than the predicted additive value, hereinafter referred to as a Type I effect, or (ii) to a level greater than the predicted additive value, hereinafter referred to as a Type II effect.

Thus, Type I and Type II effects are terms used to refer to the level of increase in signal or signal:background ratio, the Type II effect being the best example of synergy.

The background level of luminescence can be decreased to a level lower than that of either of the individual enhancers at that concentration. This is also described as a Type I effect.

When discussing "background" levels of light output it is only relevant to discuss a Type I effect, i.e. the combination of enhancers lowering the level of background luminescence to a level below that of either of the individual enhancers. The concept of additive value is irrelevant when discussing the lowering of background luminescence and therefore there is no equivalent to a Type II effect.

By definition, each of the enhancers individually is required to increase the signal or the signal:background ratio, relative to the unenhanced reaction, under at least one set of conditions. However, the combination is required to produce either enhancement as defined above, i.e. the type I or type II effect, relative to the reaction carried out with only one enhancer, or a decrease in background.

The various type I and II effects can be easily understood by way of illustration with two enhancers E1 and E2.

BACKGROUND LUMINESCENCE

A. The background light emission may be reduced to a value lower than that obtained with either enhancer individually.

| eg, | background light emission (relative light units) |
|---|---|
| E1 (enhancer 1) | 100 |
| E2 (enhancer 2) | 50 |
| E1 + E2 (mixture) | 40 |

SIGNAL

A. The light emission in the presence of peroxidase may be increased to a value higher than the signal obtained with either enhancer individually (a Type I effect).

| eg, | signal (relative light units) |
|---|---|
| E1 | 1000 |
| E2 | 500 |
| E1 + E2 | 1200 |

B. The light emission in the presence of peroxidase may be increased to a value higher than the predicted additive value of the individual enhancers in combination (a Type II effect).

| eg, | signal (relative light units) |
|---|---|
| E1 | 1000 |
| E2 | 500 |
| E1 + E2 | 2900 |

SIGNAL/BACKGROUND (S/B) RATIO

A. The signal/background ratio in the presence of peroxidase may be increased to a value higher than the signal/background ratio obtained with either enhancer individually (a Type I effect).

| eg, | signal/background |
|---|---|
| E1 | 44 |
| E2 | 15 |
| E1 + E2 | 52 |

B. The signal/background In the presence of peroxidase may be increased to a value higher than the predicted additive value of the signal/background ratio of the individual enhancers in combination (a Type II effect).

| eg, | signal/background |
|---|---|
| E1 | 44 |
| E2 | 15 |
| E1 + E2 | 87 |

The combinations of chemiluminescence enhancers of use in the present invention consist of or include an organoboron enhancer together with a non-boron enhancer.

The organoboron enhancer may be any organic compound containing at least one boron atom and which is capable of enhancing the above-described chemiluminescent reaction. Preferably it contains a benzene ring linked to the boron atom and most preferably it is a ring-substituted phenylboronic acid. The preferred organoboron enhancers are compounds of formula (I)

in which the R groups are the same and each is selected from the group consisting of hydrogen, n-butyl, 4'-chlorophenyl and 3',5'-dichlorophenyl; or the Rs together are 0,0-propylene (thereby forming with the boron atom, a cyclic ether);

W is selected from the group consisting of hydrogen, methyl, methoxy, hydroxy and chloro;

X is selected from the group consisting of hydrogen, chloro, amino and nitro;

Y is selected from the group consisting of hydrogen, methyl, carboxy, chloro, bromo, iodo, phenyl, phenoxy, 4'-chloroanilino, 4'-boronylphenyl, 4'-bromophenyl, 2'-carboxyethenyl and trimethylsilyl;

Z is selected from the group consisting of hydrogen, 5-chloro, 5-bromo, 5-(3'-trifluoromethyl)phenylazo and 6-chloro; or W and X together may represent a fused benzene ring and X and Y together may represent a fused benzene ring substituted by hydroxy in the 6 position of the naphthalene ring numbering, provided that (1) when each R is hydrogen:
 (a) W, X, Y, Z are each hydrogen; or
 (b) W, X and Z are each hydrogen and Y is selected from the group consisting of iodo, bromo, chloro, trimethylsilyl, phenoxy, phenyl, 4'-chloroanilino, methyl, 4'-boronylphenyl and 2'-carboxyethenyl; or
 (c) W and Z are each hydrogen and:
  (i) X and Y together represent a fused benzene ring substituted by hydroxy in the 6-position of the naphthalene ring numbering; or
  (ii) X is either nitro and chloro and Y is chloro: or
  (iii) X is nitro and Y is carboxy;

(d) W, Y and Z are each hydrogen and X is amino, chloro or nitro; or (e) W and X together represent a fused benzene ring and Y and Z are each hydrogen; or (f) X and Y are each hydrogen and:
  (i) W is methoxy and Z is 5-bromo; or
  (ii) W is hydroxy and Z is 5-(3'-trifluoromethyl)phenylazo; or
  (iii) W is methyl and Z is hydrogen;

(g) W is chloro, X is chloro and Y and Z are each hydrogen; or (h) W and Y are each chloro, X is amino and Z is 6-chloro;

(2) when each R is n-butyl, W, X and Z are each hydrogen and Y is bromo or 4'-bromophenyl;

(3) when each R is 4'-chlorophenyl W, X and Z are each hydrogen and Y is chloro;

(4) when each R is 3',5'-dichlorophenyl, W and Y are each hydrogen, X is chloro and Z is 5-chloro; and

(5) when the Rs together represent O,O-propylene, X, Y and Z are each hydrogen; and the compounds bis(catechol)borate, boroglycine, pentaerythritol borate, 4-(3'-borono-4'-hydroxyphenylazo)benzoic acid, diphenylisobutoxyborane, diphenylboronic anhydride and dimethylphenylboronic acids.

Particularly preferred organoboron enhancers comprise: para-iodophenylboronic acid, para-bromophenylboronic acid, 4-biphenylboronic acid, 4-(trimethylsilyl)benzeneboronic acid, 2-hydroxy-5-[(3'-trifluoromethyl)phenylazo] benzeneboronic acid, boroglycine, 4-chloro-3-nitrophenylboronic acid, 4-chlorophenylboronic acid, 4-(2'-carboxyethenyl)phenylboronic acid, 4-(4'-bromophenyl)phenyl-di-n-butoxyborane, 4-chlorophenyl-di-( 4'-chlorophenoxy)borane, 4,4'-bis(phenylbornonic acid), diphenylboronic anhydride, 4-(4'-chloroanilino)phenylboronic acid and 4-bromophenyl-di-n-butoxyborane.

The phenolic enhancers include compounds of formula (II)

wherein:
(i) A and Q are hydrogen; and
  $R_1$ is (a) halogen; (b) phenyl; (c)

$R_2$ being —$CH_2$—, —O— or —N=N— and V being hydrogen or $R_2$ being —O—, —S— or —S—S— and V being hydroxy;
(d)

(e)

(f) —CH=CH—$R_3$, $R_3$ being carboxy or 2,4-dinitrophenyl;
(g) —$CH_2CH_2COOC_2H_5$; or $C_1$-$C_6$ alkyl;
(j) imidazol-1-yl or benzimidazol-2-yl;
(k) 4-thiazolyl, 4-oxazolyl or 4-imidazolyl, each of which may be ring-substituted;
(l) 4-acetamido; and
(m) 1,2,3,4-thiatriazolyl-5-amino;

(ii) A is hydrogen;
  Q is halogen or $C_{1-6}$ alkyl; and
  $R_1$ is halogen;

(iii) A is halogen;
  Q is hydrogen; and
  $R_1$ is halogen or phenyl; or (iv) A is hydrogen or halogen;
  $R_1$ is —$S(CH_2)_n$—$R_4$ wherein n represents an integer of 1 to 5; $R_4$ represents hydrogen, cyano, morpholino, carboxylic acid, an alkoxycarbonyl group of 2 to 7 carbon atoms, metallic carboxylate, amido, aldehyde, or allyl, or is a phenyl group, which may be substituted by a halogen atom; or
  $R_1$ and Q together represent a naphthalene nucleus-completing chain which, read in the direction from $R_1$ to Q, is of formula $R_5$ being hydrogen or halogen, whereby the compound of formula (II) is a beta-naphthol of formula (VI):

and "halogen" in every occurrence in (i), (ii), (iii) and (iv) above means chlorine, bromine or iodine.

Preferably the phenolic enhancer is selected from the group consisting of the compounds 4-chlorophenol, 4-bromophenol, 4-iodophenol, 4-bromo-2-chlorophenol, 2,4-dichlorophenol, 3,4-dichlorophenol, 4-methylphenol, 4-tert-butylphenol, ethyl 3-(4-hydroxyphenyl)propionate, 4-benzylphenol, 4-(2',4'-dinitrostyryl) phenol, 4-hydroxycinnamic acid, 4-phenylphenol, 2-chloro-4-phenylphenol, 4-(4'-hydroxyphenyl)benzophenone, 4-(phenylazo) phenol, 4-(2'-carboxyphenylazo)phenol, 4-phenoxyphenol, 4-(4'-hydroxyphenoxy)phenol, 4-hydroxyphenyl sulphide, 4-hydroxyphenyl disulphide, (4-cyanomethylthio)phenol, 4-cyanomethylthio-2-fluorophenol, 4-cyanomethylthio-2-chlorophenol, 4-cyanomethylthio-2-bromophenol, 4-imidazol-1-ylphenol, naphth-2-ol, 1-bromonaphth-2-ol, 6-bromonaphth-2-ol and 1,6-dibromonaphth-2-ol.

The most preferred phenol enhancers comprise:
  4-iodophenyl, 4-hydroxycinnamic acid and 4-imidazol-1-ylphenol, 4-phenylphenol and 4-bromophenol.

The above-mentioned organoboron enhancers are those described in above-mentioned U.K. Patent Application No. 2265459 A The above-mentioned phenolic enhancers are those described in above-mentioned European Patent No. 116454 B, U.K. Patent 2205954 B and European Patent Application Publications Nos. 384271 A, 455471 A and 505198 A, and U.S. Pat. No. 5,279,940, the contents of which in relation to enhancers and their formulation are herein incorporated by reference.

Other enhancers which can be used are any of those mentioned in the other patent references cited above, including, for example amine enhancers according to U.K. Patent 2162946 B, the contents of which in relation to enhancers and their formulation are herein incorporated by reference.

The preferred combinations of enhancers are a preferred organoboron enhancer in combination with a preferred phenolic enhancer. Particularly favoured combinations are those where the organoboron enhancer is 4-biphenylboronic acid, 4-iodophenylboronic acid, trans-4-(2'-carboxyethenyl)phenylboronic acid or 4-bromophenylboronic acid and the phenolic enhancer is 4-phenylphenol, 4-iodophenol, 4-hydroxycinnamic acid or 4-bromophenol.

Depending on the experimental procedure or assay being performed emphasis will be placed on either improved signal or signal:background ratio or possibly on a beneficial decrease in background luminescence.

For example, low background light emission from a luminol-peroxide assay reagent is desirable because assay reagent background is a major factor limiting the detection limit for peroxidase in this type of chemiluminescent assay.

High signals in the presence of peroxidase are desirable because the measurement of high light levels is simple and convenient (e.g. a wide range of light emission detectors can be used—photographic film, silicon photodiodes).

An increased signal/background ratio in a peroxidase assay improves assay sensitivity and hence the ability to discriminate between incremental amounts of peroxidase.

An increase in signal/background ratio can be achieved in a number of ways. Signal may be increased, background may be decreased, or there may be combinations of these effects. For example, an increased signal to background ratio can be obtained from a combination of enhancers that lower the signal in the presence of peroxidase, but produce a major reduction in the assay background.

While the invention applies to improvements in any chemiluminescent reaction involving the above-stated reaction partners, for any purpose, it is primarily of interest in connection with an assay, especially immunoassay e.g. to assay an antigen or antibody. The term "assay" herein covers detection, semi-quantitation and quantitation. Typically, the assay is carried out so that the light output is relatable to the amount of peroxidase employed, the peroxidase then being the substance directly determined. Similarly, if the substance to be determined is another of the reaction partners, the "signal" denotes the presence of the substance to be determined, the "background" its absence.

Although the invention is usable to determine the presence or amount of any one of the four above-stated reaction partners, such a reaction partner is not necessarily itself the substance to be assayed. Thus, the oxidant can be produced as a result of an earlier reaction or cascade of earlier reactions carried out on a sample. The peroxidase or the FADCH can be in the form of a conjugate to, say, an antibody which is used in an immunoassay to determine an antigen. The invention is accordingly applicable to any method of diagnostic assay of a substance, the presence or amount of which is relatable to the presence or amount of a reaction partner selected from the group consisting of a FADCH, a peroxidase enzyme, an oxidant and an enhancer which together are reactable in a chemiluminescent reaction and wherein the reaction is carried out, the light output is detected or measured and thence the presence or amount of the substance to be assayed is related to the light output.

The improvement in signal:background ratio is of importance in controlling the sensitivity of chemiluminescent assays. The enhancers of the present invention are therefore of particular use in those situations where a high degree of sensitivity is required, for example in blotting assays. Thus the present invention is of especial use in blotting assays including Western, Southern and Northern blotting assays, as well as dot blots and other nucleic acid hybridisation assays.

The best results are obtained at higher pH. Preferably the pH is in the range 7.5 to 9 at the time of mixing all the reagents.

Any chemiluminescent fused aromatic diacyl cyclic hydrazide (FADCH) can be used in the invention, that is to say any FADCH which is oxidisable in the presence of a peroxidase catalyst by an added oxidant to give chemiluminescence can be used. Preferably the FADCH is one in which the aromatic residue consists of or includes a benzene ring which may be substituted in any way appropriate to produce chemiluminescence, usually by an amino or substituted amino group. When the aromatic moiety is benzenoid, the FADCH is a dihydrophthalazinedione (DPD). Examples of DPDs can be found in the above-mentioned patent specifications and include luminol (the most preferred) isoluminol, 6-(N-4-aminobutyl-N-ethyl)amino-2,3-dihydrophthalazinedione (ABEI), 6-(N-6-aminohexyl-N-ethyl) amino-2,3-dihydrophthalazinedlone (AHEI) and 7-dimethylaminonaphthalene-1,2-dicarboxylic acid hydrazide. Alternatively, the FADCH may be one in which the aromatic residue is non-benzenoid, especially a pyridinoid residue, e.g. as in the pyridopyridazine compounds of formula (VII)

wherein $R_a$ is a hydrocarbon group or a heterocyclic group each of which may be substituted and $R_b$ is hydroxy group, thiol group, amino group or a mono-substituted amino group, and when $R_b$ is a monosubstituted amino group, $R_b$ may be taken together with $R_a$ to form a ring; $R_c$ is hydrogen atom, a hydroxy group which may be substituted, an amino group which may be substituted, a thiol group which may be substituted, a halogen atom, a heterocyclic group, nitro group, cyano group, carboxyl group which may be esterified or amidated, azido group, sulfo group or an organic sulfonyl group, provided that when $R_a$ is an aliphatic group $R_c$ is not hydrogen atom; and D is oxygen atom or sulfur atom or a salt thereof, described in European Patent Application 491477A (Takeda Chemical Industries Ltd.), the contents of which are hereby incorporated by reference, especially 7-[4-(3-aminopropyloxy) phenyl]-8-hydroxypyrido[3,4-d]pyridazine-1,4-dione, of which luminol is normally preferred. The FADCH can be free or conjugated to a ligand to provide a direct label. Such luminophore-labelled assays are known in the art.

The oxidant can be any added substance (not oxygen from the air) which oxidises the FADCH in a light-emitting reaction; hydrogen peroxide is usual, but a perborate, such as the sodium salt, is an alternative. Generally stated, the oxidant concentration is desirably in the range 0.5 micromoles to 300 millimoles/liter, preferably 10 to 200 millimoles/liter.

The peroxidase enzyme will normally be HRP and of a grade appropriate to use in luminescent assays. Preferably the HRP is a basic isoenzyme, for example of Sigma Type VIA or IX. It can be free or conjugated to a ligand. Microperoxidase is not normally suited to labelled peroxidase assays, but may be used when one of the other reaction partners is labelled. The peroxidase enzyme may be used as a label by direct conjugation, e.g. to an antibody, or it may be conjugated to avidin or streptavidin, whereby the biotin: avidin/streptavidin binding interaction may be used to enhance the labelling.

The concentrations of the reaction partners of the chemiluminescent reaction will depend on the nature of the assay being carried out and particularly on which of them is being assayed. Generally stated, the light output is greater, the greater the concentration of FADCH. Thus, when peroxidase or oxidant is being assayed, the use of excess FADCH is recommended. Generally stated, the FADCH concentration is desirably from 0.5 micromole to 200 millimoles per liter preferably 0.05 to 200 millimoles/liter, most preferably 0.1 to 1 millimole/liter.

The concentration of peroxidase is of interest if peroxidase is not the reaction partner being assayed. Excess peroxidase does not normally have a marked effect on light intensity, the peroxidase being a catalyst which is recycled. Where luminol or the oxidant is being assayed, therefore, the peroxidase need only be present in a modest concentration, such as 0.01 microgram to 5000 mg/liter, preferably not more than 50 mg/liter, but depending on the activity of the peroxidase per gram.

The concentration of the individual enhancers will usually be in the range 0.01 micromole to 4 moles/liter, preferably 10 micromoles to 100 millimoles/liter. It is believed that the enhancer or a species or derivative thereof competes with the FADCH in the reaction and it is therefore desirable to optimise the relative concentrations of the enhancer(s) and the FADCH. Typically, the FADCH is present at a 1.25 to 20 times molar excess of one of the enhancers.

As is evident from the Examples that follow, the concentrations of the individual enhancers may be varied to best bring about the desired improvement in the chemiluminescent reaction, e.g. the total combination of the enhancers or the relative concentration of each enhancer may be adjusted to decrease the background luminescence, or improve the signal output or the signal:background ratio. These variations are well within the ability of the skilled artisan and the desired effect will be obtained with a minimum of trial and error.

In brief, all conditions and features of the chemiluminescent reactions, the reaction partners thereof, applications of the assay and so on (except where inconsistent with the above description) can be as set forth in European Patent No. 116454 B, the disclosure of which in relation thereto is herein incorporated by reference.

EXAMPLES

Abbreviations Used and Other Explanations
Organoboron Enhancers
K 4-Biphenylboronic acid=4-phenylylboric acid
PIBA 4-Iodophenylboronic acid PHCBA Trans-4-(3-propenoic acid)phenylboronic acid= trans-4-(2'-carboxyethenyl )phenylboronic acid
PBBA 4-Bromophenyl boronic acid
Phenol Enhancers
PHD 4-Phenylphenol
PBP 4-Bromophenol
PHCA 4-Hydroxycinnamic acid
PIP 4-Iodophenol
4-AP 4-Acetamidophenol
6-BN 6-Bromo-2-naphthol 2,4-DCP 2,4-Dichlorophenol
Amine Enhancers
4-MA 4-Anisidine=4-methoxyaniline
TMB N,N,N', N'-tetramethylbenzidine The luminescence values are of light output in arbitrary units (hv).

S=signal (with peroxidase)

B=background (without peroxidase)

S/B=signal: background ratio

The expression "diluted 1:n", where n is a specified number, means that 1 part of the concentrated solution is diluted with n−1 parts of diluent to give n parts of diluted solution, all parts by volume. The degrees of dilution ignore fractions of a ml. of concentrated solution. Thus, 50.5 ml diluted 1:10 means that it is made up to 500 ml with the diluent.

γ=yes; N=no

A=concentration of stock solution

"Amerlite" is a Registered Trade Mark.

EXAMPLE 1

Standard Procedure for Measuring Signal and Background Chemiluminesence

Stock solutions of PHCBA (10 mmol/l) and PHCA (10 mmol/l) were prepared in DMSO, and diluted in Tris buffer (0.1 mol/l, pH 8.6). The luminol-hydrogen peroxide reagent was prepared as follows: sodium luminol (12.5 mg) was dissolved in 50 ml of Tris buffer (0.1 mol/l, pH 8.6), and 15.5 μl of hydrogen peroxide (30% w/v) was mixed with 0.5 ml of Tris buffer (0.1 mol/l, pH 8.6). These two solutions were combined and diluted 1:10 in Tris buffer (0.1 mol/l, pH 8.6). 10 μl of PHCA (0–10 mmol/l), 10 μl of PHCBA (0–1 mmol/l), and 100 μl of luminol-peroxide were mixed in a microwell and the light emission was measured using the Amersham plate reader.

This reading provides the BACKGROUND level of chemiluminescence.

The experiment was repeated, except that a sample of horseradish peroxidase (HRP) (10 μl, 1:10,000 dilution of a 1 mg/ml stock solution in the same Tris buffer) was also added to the microwell.

The light emission measured using the Amersham plate reader provides the SIGNAL level of chemiluminescence. The SIGNAL:BACKGROUND ratio is then simply derived.

EXAMPLE 2

Combinations of Enhancers that Produce a Type I Effect (Reduction) in Background Luminescence Background luminescence was measured as described in Example 1 using the combinations of enhancers listed in Table 1.

In Table 1, E1 and E2 are the two enhancers, one (E1) an organoboron enhancer and the other (E2) a phenol enhancer. Column V/A shows the volume and concentration of the E1 enhancer solution before it is added to the assay tube. In each assay 10 μl of a 1 mM stock solution of each E2 enhancer was added. E1+E2 is the combination of the two enhancers. The combination comprised a mixture of the enhancers E1 and E2 at the concentrations used when tested individually.

For each combination E1+E2 the background luminescence was lower than either E1 or E2 when used individually, i.e. a Type I effect.

units of the enhancer or combination. In the combination E1+E2, 10 μl of each enhancer was added to the assay.

For each combination a Type II effect was observed, i.e. the light output of E1+E2 was greater than the sum of the values observed for E1 and E2 individually.

TABLE 1

Combinations of organoboron and phenolic enhancers

| E1 | V/A | hv | E2 | hv | E1 + E2 | hv |
|---|---|---|---|---|---|---|
| PIP | 20 μl/10 mM | 0.01316 | K | 0.103 | PIP + K | 0.01259 |
| K | 20 μl/10 mM | 0.01688 | PHCA | 0.03805 | K + PHCA | 0.00687 |
| K | 20 μl/10 mM | 0.00944 | PBP | 0.04606 | K + PBP | 0.00629 |
| PHD | 20 μl/10 mM | 0.00601 | K | 0.08068 | PHD + K | 0.00515 |
| PHCBA | 20 μl/10 mM | 0.01574 | PIP | 0.03805 | PHCBA + PIP | 0.00887 |
| PHCBA | 20 μl/10 mM | 0.01545 | PHCA | 0.03004 | PHCBA + PHCA | 0.0085 |
| PHCBA | 20 μl/10 mM | 0.01774 | PBP | 0.05779 | PHCBA + PBP | 0.01001 |
| PHCBA | 20 μl/10 mM | 0.02375 | PHD | 0.05722 | PHCBA + PHD | 0.01202 |
| PIBA | 20 μl/10 mM | 0.01459 | PIP | 0.07124 | PIBA + PIP | 0.01259 |
| PHCA | 10 μl/10 mM | 0.00916 | PIBA | 0.06836 | PHCA + PIBA | 0.00629 |
| PIBA | 20 μl/10 mM | 0.02432 | PBP | 0.06323 | PIBA + PBP | 0.02003 |
| PHD | 20 μl/10 mM | 0.00744 | PIBA | 0.02289 | PHD + PIBA | 0.00658 |
| PIBA | 20 μl/10 mM | 0.01631 | PIP | 0.08755 | PIBA + PIP | 0.00916 |
| PBBA | 20 μl/10 mM | 0.0555 | PHCA | 0.01516 | PBBA + PHCA | 0.00572 |
| PBBA | 20 μl/10 mM | 0.01087 | PBP | 0.0658 | PBBA + PBP | 0.00687 |
| PBBA | 20 μl/10 mM | 0.01173 | PHD | 0.05007 | PBBA + PHD | 0.00744 |

EXAMPLE 3

Combinations of Enhancers That Produce a Type II Effect (Increase) on the Signal in a Chemiluminescent Reaction

TABLE 2

| E1 | A | hv | E2 | A | hv | E1 + E2 | hv |
|---|---|---|---|---|---|---|---|
| Boronate + Phenol | | | | | | | |
| K | 1 mM | 131.66 | PIP | 0.01 mM | 1.39334 | K + PIP | 138.375 |
| K | 1 mM | 76.1195 | PHCA | 0.02 mM | 3.1735 | K + PHCA | 97.9878 |
| K | 0.5 mM | 81.2039 | PBP | 0.1 mM | 1.21624 | K + PBP | 96.2557 |
| K | 0.02 mM | 14.3445 | PHD | 0.01 mM | 53.6945 | K + PHD | 71.7129 |
| PHCBA | 1 mM | 7.05568 | PIP | 0.01 mM | 0.78422 | PHCBA + PIP | 9.0627 |
| PHCBA | 0.1 mM | 3.39952 | PHCA | 0.01 mM | 3.86187 | PHCBA + PHCA | 8.07507 |
| PHCBA | 1 mM | 11.7592 | PBP | 0.01 mM | 0.68437 | PHCBA + PBP | 16.5538 |
| PHCBA | 0.1 mM | 6.38132 | PHD | 0.01 mM | 55.2709 | PHCBA + PHD | 96.4259 |
| PIBA | 10 mM | 65.9178 | PIP | 0.01 mM | 1.05201 | PIBA + PIP | 69.5116 |
| PIBA | 0.2 mM | 3.92567 | PHCA | 0.01 mM | 2.94633 | PIBA + PHCA | 8.26104 |
| PIBA | 1 mM | 4.58658 | PBP | 0.2 mM | 4.43952 | PIBA + PBP | 11.625 |
| PIBA | 0.05 mM | 0.25607 | PHD | 0.1 mM | 76.6434 | PIBA + PHD | 83.2209 |
| PBBA | 0.01 mM | 0.36278 | PIP | 0.5 mM | 49.3236 | PBBA + PIP | 50.7799 |
| PBBA | 0.01 mM | 0.40656 | PBP | 1 mM | 47.7276 | PBBA + PBP | 56.3306 |
| PBBA | 0.2 mM | 0.37709 | PHD | 0.1 mM | 73.986 | PBBA + PHD | 89.7591 |

The signal level of chemiluminescence was measured as described in Example 1 using the combinations of enhancers listed in Table 2.

In Table 2, E1 is the organoboron enhancer and E2 is the phenolic enhancer. Columns A show the concentration of stock solution of enhancer, 10 μl of which was used in each assay. The "hv" columns show the light output in arbitrary

EXAMPLE 4

Combinations of Enhancers That Produce a Type II Effect on Signal Background Ratio The signal:background ratio was calculated as described in Example 1 for the combinations of enhancers listed in Table 3.

In Table 3, E1 is the organoboron enhancer and E2 the phenolic enhancer. Columns A show the concentration of stock solution of enhancer, 10 μl of which was used in each assay. S/B shows the signal:background ratio for each enhancer or combination.

In the combination E1+E2, 10 μl of each enhancer was added to the assay.

For each combination, a Type II effect on the signal:background ratio was observed.

TABLE 3

| E1 | A | S/B | E2 | A | S/B | E1 + E2 | S/B |
|---|---|---|---|---|---|---|---|
| Boronate + Phenol | | | | | | | |
| K | 1 mM | 1316.6 | PIP | 0.01 mM | 7.0 | K + PIP | 1441.5 |
| K | 0.5 mM | 1888.4 | PBP | 0.1 mM | 23.9 | K + PBP | 2238.6 |
| K | 0.02 mM | 75.5 | PHD | 0.01 mM | 282.6 | K + PHD | 377.4 |
| K | 1 mM | 211.4 | PHCA | 0.02 mM | 32.3 | K + PHCA | 326.6 |
| PHCBA | 2 mM | 257.9 | PIP | 0.01 mM | 9.2 | PHCBA + PIP | 362.1 |
| PHCBA | 0.1 mM | 18.9 | PHCA | 0.01 mM | 27.6 | PHCBA + PHCA | 53.9 |
| PHCBA | 1 mM | 183.8 | PBP | 0.01 mM | 6.8 | PHCBA + PBP | 285.3 |
| PHCBA | 0.1 mM | 33.6 | PHD | 0.1 mM | 769.5 | PHCBA + PHD | 994.1 |
| PIBA | 0.5 mM | 98.0 | PIP | 0.01 mM | 7.5 | PIBA + PIP | 135.9 |
| PIBA | 0.1 mM | 6.4 | PHCA | 1 mM | 273.8 | PIBA + PHCA | 345.7 |
| PIBA | 2 mM | 47.7 | PBP | 1 mM | 531.1 | PIBA + PBP | 872.0 |
| PIBA | 0.05 mM | 5.7 | PHD | 0.1 mM | 1630.6 | PIBA + PHD | 2190.0 |
| PBBA | 1 mM | 5.5 | PIP | 2 mM | 1799.3 | PBBA + PIP | 2435.4 |
| PBBA | 1 mM | 4.3 | PHCA | 1 mM | 176.2 | PBBA + PHCA | 270.5 |
| PBBA | 1 mM | 4.6 | PBP | 2 mM | 895.1 | PBBA + PBP | 1577.7 |
| PBBA | 2 mM | 7.3 | PHD | 0.1 mM | 831.3 | PBBA + PHD | 3293.3 |

SUMMARY OF EXAMPLES 2 to 4

Tables 4 and 5 below summarise the data of Examples 2 to 4. Table 4 is directed to whether the combinations display a Type I effect, and Table 5 is directed to whether the combinations display a Type II effect. In each Table three symbols appear for each combination in the order background, signal, signal:background ratio. The symbols used are Y=yes, N=no, *=not applicable. A positive response (Y) is given if a Type I or Type II effect occurs at at least one concentration of the combination.

TABLE 4

| Does the combination display a Type I effect? | | | | |
|---|---|---|---|---|
| Organoboron | Phenolic enhancer | | | |
| enhancer | PIP | PHD | PBP | PHCA |
| PIBA | Y,Y,Y | Y,Y,Y | Y,Y,Y | Y,Y,Y |
| K | Y,Y,Y | Y,Y,Y | Y,Y,Y | Y,Y,Y |
| PBBA | Y,Y,Y | Y,Y,Y | Y,Y,Y | Y,Y,Y |
| PHCBA | Y,Y,Y | Y,Y,Y | Y,Y,Y | Y,Y,Y |

TABLE 5

| Does the combination display a Type II effect? | | | | |
|---|---|---|---|---|
| Organoboron | Phenolic enhancer | | | |
| enhancer | PIP | PHD | PBP | PHCA |
| PIBA | *,Y,Y | *,Y,Y | *,Y,Y | *,Y,Y |
| K | *,Y,Y | *,Y,Y | *,Y,Y | *,Y,Y |
| PBBA | *,Y,Y | *,Y,Y | *,Y,Y | *,Y,Y |
| PHCBA | *,Y,Y | *,Y,Y | *,Y,Y | *,Y,Y |

EXAMPLE 5

A. An Enhanced Assay for Peroxidase Displaying a Type II Effect

The effect of 4-biphenylboronic acid (K) on the 4-iodophenol (PIP)-luminol-peroxide reaction and on Amerlite Signal Reagent (ASR) (believed to contain PIP as the enhancer) was investigated.

Effect of K on HRP-Catalyzed Luminol Peroxide-PIP Reaction

The luminol-hydrogen peroxide reagent was prepared as follows. Sodium luminol (12.5 mg) was dissolved in 50 ml of Tris buffer (0.1 mol/l, pH 8.6), and 15.5 μl of hydrogen peroxide (30% w/v) was mixed with 0.5 ml of Tris buffer (0.1 mol/l, pH 8.6). These two solutions were combined and diluted (1:10 dilution). A stock solution of K and PIP (10 mmol/l) was prepared in DMSO and dilutions were prepared in 0.1 mol/l Tris buffer, pH 8.6). The luminol-hydrogen peroxide reagent (100 μl), 10 μl of PIP (0.1 mmol/l), and either 10 μl of K (0.005–1 mmol/l), or as a control, 10 μl of Tris buffer (0.1 mol/l, pH 8.6) were mixed in a microwell. The light emission was monitored for 25 minutes.

Figure 1:
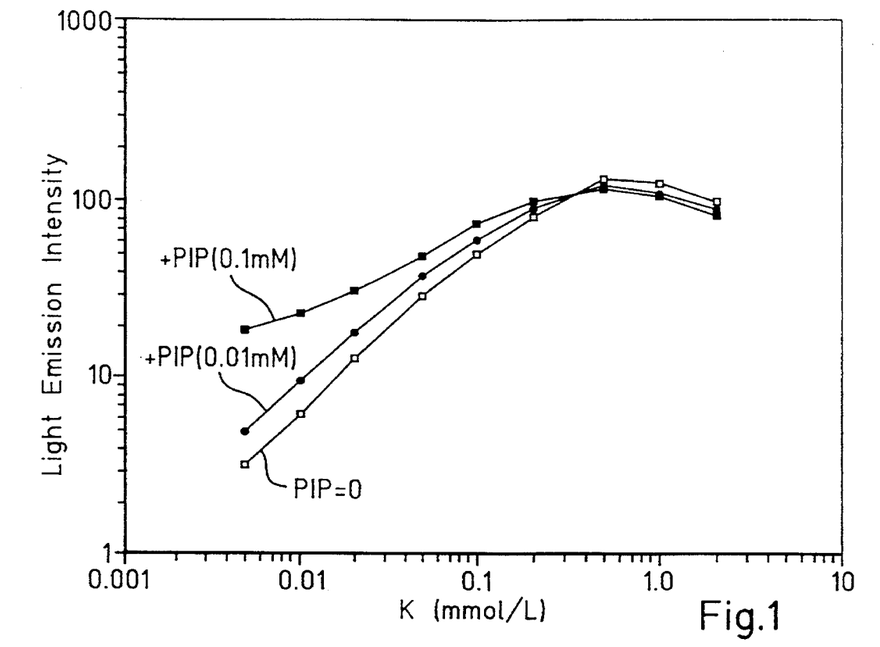
FIG. 1 shows plots of light emission (signal) intensity against concentration of organoboron enhancer ("K") for different concentrations of phenolic enhancer ("PIP")

FIG. 1 shows the effect of K on a PIP-enhanced reaction to detect HRP. The concentration of K is shown along the x-axis in mmol/l and signal light output (in arbitrary units) is shown along the y-axis (log scale).

B. Detection Limit and Standard Curve for HRP

Samples (10 μl) of dilutions of a stock solution of HRP Type VI-A (1 mg/ml in Tris buffer, pH 8.6) were analyzed using 100 μl of Amerlite signal reagent (ASR), containing 4-phenylboronic acid (final concentration 25 μmol/l).

Figure 2:
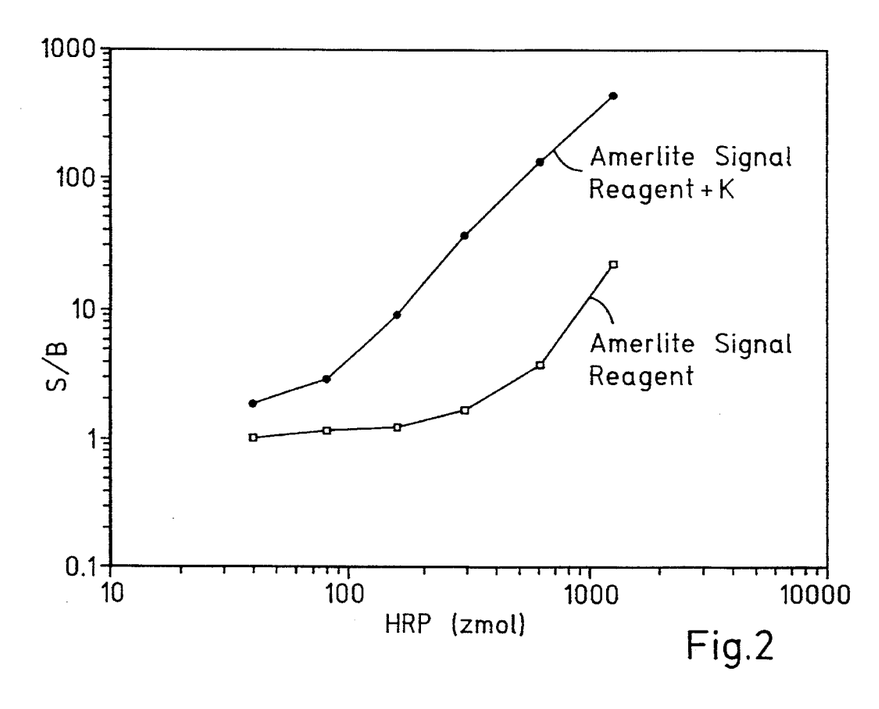
FIG. 2 shows plots of the signal/background ratio against peroxidase concentration, firstly using a conventional phenolic enhancer ("Amerlite Signal Reagent") and secondly with the addition thereto of an organoboron enhancer 9"K").

FIG. 2 shows the standard curves for HRP determined using the conventional (ASR) or synergistically enhanced reagent. In FIG. 2 the concentration of HRP in zeptomoles ($1 \times 10^{-21}$ moles) is shown on the x-axis and signal:background ratio is shown on the y-axis. The detection limit for HRP using the synergistically enhanced end-point was 19.5 zeptomoles ($19.5 \times 10^{-21}$ moles), and this is believed to be the most sensitive HRP assay described thus far.

EXAMPLE 6

Synergistic Enhanced Enzymeimmunoassay for Thyrotropin (a Type II Effect

A synergistically enhanced (K) peroxidase assay described in Example 5 was compared with the conventional end-point in two different TSH enzymeimmunoassays.

TSH assay kits and TSH-30 assay kits were purchased from Kodak Clinical Diagnostics (Rochester, N.Y.). Clinical specimens, previously analyzed for TSH using Bio-Rad (Richmond, Calif.) TSH kit, were used for the method comparison studies.

Optimization of 4-Biphenylboronic Acid (K) Concentration in the Amerlite Signal Reagent The effect of different amounts of K on the detection of HRP using the Amerlite signal reagent (ASR) was tested in order to determine the optimum (kinetics and signal) concentration of K (data not shown). ASR contains 4-iodophenol as the enhancer. Thus the use of K with ASR provides a combination of enhancers demonstrated above to give a Type II effect. A concentration 1.01 mmol/l of K was chosen for the TSH assay.

Kodak Amerlite TSH Assay

All assays were performed according to the manufacturer's instructions. Standard curves were analyzed in duplicate and clinical specimens were analyzed as singletons. Each TSH assay was performed using both the conventional and synergistically enhanced assay reagent (10 µl, 0.1 µmol/1, 4-biphenylboronic acid/100 µl ASR).

Kodak Amerlite TSH-30 Ultrasensitive Assay

All assays were performed according to the manufacturer's instructions. Standard curves were analyzed in duplicate and clinical specimens were analyzed as singletons. Each TSH assay was performed using both the conventional and synergistically enhanced assay reagent (10 µl, 0.1 µmol/1, 4-biphenylboronic acid/100 µl ASR).

TSH Detection Limits

Detection limits were determined by two different methods.

I. The zero standard was analyzed in replicate (n=20) and the detection limit determined from the mean +2 SD based on a two point standard curve using the zero and the lowest standard (mean values).

II. The zero standard was analyzed in replicate (n=20) and the detection limit determined from the mean +2 SD based on a two point standard curve using the zero and a 1:40 dilution of the lowest standard (mean values).

Assay Performance

Comparison of TSH values on clinical samples obtained using the two different end-points showed good agreement as shown in Table 6 below.

TABLE 6

Comparison of serum TSH measured using Kodak Amerlite TSH and TSH-30 assay with a conventional and a synergistically enhanced end-point

|  |  | TSH assay | TSH-30 assay |
|---|---|---|---|
| number of samples |  | 29 | 29 |
| correlation equation | A | Y = 0.191 + 0.97X | Y = 0.01 + 0.82X |
|  | B | Y = −0.014 + 0.86X |  |
|  | C |  | Y = 0.027 + 1.09X |
| correlation coefficient | A | 0.98 | 1.0 |
|  | B | 1.0 |  |
|  | C |  | 1.0 |

A, BioRad TSH assay versus Amerlite TSH assay and TSH-30 assay both synergistically enhanced
B, Amerlite TSH assay versus Amerlite TSH assay synergistically enhanced
C, TSH-30 assay versus TSH-30 assay synergistically enhanced.

The detection limit for TSH was improved over 2-fold using the new synergistically enhanced end-point, see Table 7 below. This modified TSH assay is believed to be the most sensitive TSH assay thus far described.

TABLE 7

Comparison of detection limits for serum thyrotropin using the Kodak Amerlite TSH-30 assay with a conventional and synergistic end-point

|  | Detection Limit mIU/l |  |
|---|---|---|
| I | 0.0012 | Conventional TSH-30 assay |
| II | 0.0049 |  |
| I | 0.0005 | Synergistic TSH-30 assay |
| II | 0.0015 |  |

I, Based on 2SD of zero standard and 0.119 mIU/l standard
II, Based on 2SD of zero standard and 1/40 dilution of 0.119 mIU/l standard

EXAMPLE 7

Use of 4-Acetamidophenol with Either of Two Different Organoboron Compounds as Enhancers Stock solutions of 4-acetamidophenol (4-AP) 4-biphenylboronic acid (K) and 4-bromophenyl boronic acid (PBBA), all 1 mg/ml, in DMSO, were diluted in Tris buffer (0.1 mol/l, pH 8.6), the dilutions being as follows:

4-AP: 0, 1:10, 1:100, 1:1000

K or PBBA: 0, 1:2, 1:5, 1:10, 1:20, 1:50, 1:100 and 1:200

The procedure of Example 1 was followed, except that the enhancer solutions disclosed therein were replaced by the 4-AP, K and PBBA solutions or by both the 4-AP and K solutions or both the 4-AP and PBBA solutions.

The combination of K with 4-AP consistently gave a type I effect, giving a lower background luminescence than either K or 4-AP alone, as shown in Table 8 below. On the other hand, a type II effect, in which the signal:background ratio is synergistically greater from the combination than from the sum of that of the enhancers when used individually, was seen only at lower concentrations of K and the highest concentration of 4-AP.

Broadly similar results were obtained for the combination of PBBA with 4-AP.

TABLE 8

| K soln. | 4-AP soln. | Background hv K | Background hv 4-AP | Background hv K + 4-AP Obs. | Type I | Signal/Background K + 4-AP Calc. | Signal/Background K + 4-AP Obs. | Type II |
|---|---|---|---|---|---|---|---|---|
| 1:200 | 1:1000 | 2.23 | 1.85 | 1.73 | Y | 4.0 | 3.9 | N |
|  | 1:100 | 2.23 | 1.95 | 2.01 | N | 4.4 | 4.4 | N |
|  | 1:10 | 2.23 | 0.95 | 0.7 | Y | 16.5 | 17.8 | Y |
| 1:100 | 1:1000 | 2.10 | 1.85 | 1.58 | Y | 7.6 | 7.9 | N |
|  | 1:100 | 2.10 | 1.95 | 2.40 | N | 9.0 | 6.1 | N |
|  | 1:10 | 2.10 | 0.95 | 0.69 | Y | 20.1 | 20.2 | Y |
| 1:50 | 1:1000 | 1.74 | 1.85 | 1.43 | Y | 17.7 | 18.9 | N |
|  | 1:100 | 1.74 | 1.95 | 1.67 | Y | 19.9 | 14.9 | N |
|  | 1:10 | 1.74 | 0.95 | 0.64 | Y | 31.4 | 21.5 | N |
| 1:20 | 1:1000 | 1.57 | 1.85 | 1.48 | Y | 86 | 50 | N |
|  | 1:100 | 1.57 | 1.95 | 1.30 | Y | 86 | 47 | N |
|  | 1:10 | 1.57 | 0.95 | 0.65 | Y | 98 | 32 | N |
| 1:10 | 1:1000 | 1.19 | 1.85 | 1.11 | Y | 117 | 111 | N |
|  | 1:100 | 1.19 | 1.95 | 1.10 | Y | 117 | 82 | N |
|  | 1:10 | 1.19 | 0.95 | 0.48 | Y | 130 | 52 | N |
| 1:5 | 1:1000 | 0.80 | 1.85 | 0.75 | Y | 284 | 232 | N |
|  | 1:100 | 0.80 | 1.95 | 0.70 | Y | 284 | 223 | N |
|  | 1:10 | 0.80 | 0.95 | 0.43 | Y | 296 | 94 | N |
| 1:2 | 1:1000 | 0.46 | 1.85 | 0.43 | Y | 482 | 467 | N |
|  | 1:100 | 0.46 | 1.95 | 0.41 | Y | 482 | 415 | N |
|  | 1:10 | 0.46 | 0.95 | 0.32 | Y | 416 | 131 | N |

TABLE 9

| PBBA soln. | 4-AP soln. | Background hv PBBA | Background hv 4-AP | Background hv PBBA + 4-AP Obs. | Type I | Signal/Background PBBA + 4-AP Calc. | Signal/Background PBBA + 4-AP Obs. | Type II |
|---|---|---|---|---|---|---|---|---|
| 1:200 | 1:1000 | 0.83 | 1.21 | 0.66 | Y | 2.0 | 1.0 | N |
|  | 1:100 | 0.83 | 0.34 | 0.43 | N | 6.1 | 1.6 | N |
|  | 1:10 | 0.83 | 0.25 | 0.20 | Y | 47 | 70 | Y |
| 1:100 | 1:1000 | 0.62 | 1.21 | 0.50 | Y | 2.1 | 1.1 | N |
|  | 1:100 | 0.62 | 0.34 | 0.31 | Y | 6.1 | 1.5 | N |
|  | 1:10 | 0.62 | 0.25 | 0.15 | Y | 48 | 93 | Y |
| 1:50 | 1:1000 | 0.43 | 1.21 | 0.35 | Y | 15.5 | 1.2 | N |
|  | 1:100 | 0.43 | 0.34 | 0.23 | Y | 19.6 | 1.7 | N |
|  | 1:10 | 0.43 | 0.25 | 0.13 | Y | 61 | 28.3 | N |
| 1:20 | 1:1000 | 0.26 | 1.21 | 0.23 | Y | 2.5 | 1.5 | N |
|  | 1:100 | 0.26 | 0.34 | 0.20 | Y | 6.6 | 1.5 | N |
|  | 1:10 | 0.26 | 0.25 | 0.12 | Y | 48 | 7.7 | N |
| 1:10 | 1:1000 | 0.18 | 1.21 | 0.17 | Y | 2.8 | 1.6 | N |
|  | 1:100 | 0.18 | 0.34 | 0.14 | Y | 6.9 | 1.8 | N |
|  | 1:10 | 0.18 | 0.25 | 0.12 | Y | 49 | 2.7 | N |
| 1:5 | 1:1000 | 0.14 | 1.21 | 0.15 | N | 2.5 | 1.6 | N |
|  | 1:100 | 0.14 | 0.34 | 0.13 | Y | 6.6 | 1.8 | N |
|  | 1:10 | 0.14 | 0.25 | 0.10 | Y | 48 | 1.9 | N |
| 1:2 | 1:1000 | 0.09 | 1.21 | 0.10 | N | 2.8 | 1.7 | N |
|  | 1:100 | 0.09 | 0.34 | 0.09 | N | 6.9 | 1.7 | N |
|  | 1:10 | 0.09 | 0.25 | 0.09 | N | 49 | 1.3 | N |

EXAMPLE 8

Use of Either of Two Different Amines With an Organoboron Compound as Enhancers

Stock solutions of 4-anisidine (=4-methoxyaniline=4-MA) (10 mg/ml) N,N,N',N'-tetramethylbenzidine (=TMB) (1 mg/ml) 4-biphenylboronic acid (K) (1 mg/ml), all in DMSO, were diluted respectively 1:10,000, 1:500 and 1:20. The procedure of Example 1 was followed, except that the enhancer solutions disclosed therein were replaced by the 4-MA, TMB and K solutions or by both the 4-MA and K solutions or both the TMB and K solutions, and except that the HRP was diluted 1:500,000 instead of 1:10,000.

As seen from Table 10, the combination of enhancers gave a type II increase in signal/background ratio, either a type I (4-MA) or type II (TMB) increase in signal and a decrease in background luminescence, which is a type I effect.

TABLE 10

| Enhancer(s) | B | S | S/B |
|---|---|---|---|
| A. 4-biphenylboronic acid + 4-anisidine | | | |
| 1. 4-biphenylboronic acid | 4429 | 186628 | 42.1 |
| 2. 4-anisidine | 11200 | 32629 | 2.9 |
| 1 + 2 (calculated) | 15629 | 219257 | 45.0 |
| 1 + 2 (observed) | 4419 | 217993 | 49.3 |
| B. 4-biphenylboronic acid + N,N,N',N'-tetramethylbenzidine | | | |
| 1. 4-biphenylboronic acid | 5367 | 275062 | 51.2. |
| 2. N,N,N',N'-tetramethylbenzidine | 13579 | 35370 | 2.6 |
| 1 + 2 (calculated) | 18946 | 310432 | 53.8 |
| 1 + 2 (observed) | 2414 | 814440 | 333.2 |

EXAMPLE 9

Use of 4-(1,2,3,4-Thiatriazol-5-Ylamino)Phenol With an Organoboron Compound as Enhancers Example 8 was repeated substituting the above-captioned thiatriazolylaminophenol enhancer for 4-anisidine, with the excellent results shown in Table 11 including type II effects on signal and signal/background ratios.

TABLE 11

| Enhancer(s) | B | S | S/B |
|---|---|---|---|
| 1. 4-biphenylboronic acid | 5639 | 155056 | 27.5 |
| 2. 4-(1,2,3,4-thiatriazol-5-ylamino)phenol | 4582 | 16132 | 3.5 |
| 1 + 2 (calculated) | 10221 | 171188 | 31.0 |
| 1 + 2 (observed) | 3504 | 452572 | 129.2 |

EXAMPLE 10

Use of Perborate as an Oxidant in the Synergistically Enhanced Chemiluminescent Reaction Stock solutions of 4-biphenylboronic acid (K) (1 mg/ml) and 4-iodophenol (PIP) (10 mg/ml) were prepared in DMSO. HRP (1 mg/ml) was prepared in Tris buffer (0.1 mol/l, pH 8.6). All dilutions were made in the Tris buffer. The luminol-perborate reagent was prepared by mixing 1 ml of luminol solution (12.5 mg luminol in 50 ml of Tris buffer) with 10 μl of sodium perborate solution (27 mmol/l in Tris buffer). Luminol-perborate reagent (100 μl), containing K (10 μl, 1:20 dilution), or PIP (10 μl, 1:5000 dilution), or K and PIP was used to assay HRP (5 μl, 1:500,000 dilution). Light emission was measured for 20 minutes.

The good results shown in Table 12 show type II increases in signal and signal/background ratio.

TABLE 12

| Enhancer(s) | B | S | S/B |
|---|---|---|---|
| No enhancer: luminol-perborate | 2003 | 3205 | 1.6 |
| + K | 570 | 37045 | 65.0 |

TABLE 12-continued

| Enhancer(s) | B | S | S/B |
|---|---|---|---|
| + PIP | 1680 | 3573 | 2.1 |
| + K + PIP (calculated) | 2250 | 40618 | 67.1 |
| + K + PIP (observed) | 536 | 42064 | 78.5 |

EXAMPLE 11

Use of a Different Type of Fused Aromatic Diacyl Cyclic Hydrazide, Instead of a DPD, in the Chemiluminescent Reaction The procedure of Example 1 was followed except that the enhancers used were 4-biphenylboronic acid (K) and 4-iodophenol (PIP), the 10 mmol/liter stock solutions were diluted to various concentrations and the sodium luminol was replaced by the same weight of 8-amino-5-chloro-7-phenylpyrido[3,4-d]pyridazine- 1,4[2H,3H]dione, known as "L-012", of formula (VIII):

(VIII)

(where Ph=phenyl). In Table 13 are shown three sets of results at various dilutions. Runs A and B are typical of the best results, at dilutions giving a high signal, and a substantial type II effect on both signal and signal/background ratio. Run C exemplifies one of the less good, but still useful results, where there was a small type II effect on signal/background ratio and a small type I effect on signal.

TABLE 13

| | B | S | S/B |
|---|---|---|---|
| A. K (1:2 dilution + PIP (1:10 dilution) | | | |
| 1. K | 0.99 | 215.33 | 217.51 |
| 2. PIP | 3.22 | 7.84 | 2.43 |
| 1 + 2 (calculated) | 4.21 | 233.17 | 219.4 |
| 1 + 2 (observed) | 0.72 | 330.97 | 459.68 |
| B. K (1:5 dilution) + PIP (1:10 dilution) | | | |
| 1. K | 1.77 | 256.34 | 144.82 |
| 2. PIP | 3.22 | 7.84 | 2.43 |
| 1 + 2 (calculated) | 4.99 | 264.18 | 147.25 |
| 1 + 2 (observed) | 1.14 | 390.98 | 342.96 |
| C. K (1:50 dilution) + PIP (1:1000 dilution) | | | |
| 1. K | 2.36 | 27.45 | 9.62 |
| 2. PIP | 3.51 | 4.39 | 1.25 |
| 1 + 2 (calculated) | 5.87 | 31.84 | 10.87 |
| 1 + 2 (observed) | 2.52 | 28.86 | 11.45 |

EXAMPLE 12

Use of Different Concentrations of Fused Aromatic Diacyl Cyclic Hydrazide (Luminol) in the Chemiluminescent Reaction The procedure of Example 1 was followed except that the enhancers used were 4-biphenylboronic acid (K) and 4-iodophenol (PIP), the 10 mmol/liter stock solutions were diluted to various concentrations and the concentration of sodium luminol was increased from the 0.096 mmol/liter of the preceding Examples to 0.96 and 0.48 in two separate experiments.

From the results shown in Table 14, it will be seen that at the lower of these concentrations of luminol the type II effect on signal/background ratio extends to runs in which the concentration of organoboron enhancer is very low. Generally, the signals and backgrounds were both lower at the lower luminol concentration. These results indicate that the combination of enhancers is likely to be effective over a wide range of luminol concentrations, well below and above the range used in the Examples (approx. 0.1 to 1 mmol/liter).

TABLE 14

| Enhancer K, | mmol/l | 0.01 | 0.02 | 0.05 | 0.1 | 0.2 | 0.5 |
|---|---|---|---|---|---|---|---|
| A. Luminol concentration = 0.96 mmol/liter | | | | | | | |
| Enhancer | B | 1.35 | 1.18 | 0.91 | 1.2 | 0.57 | 0.28 |
| PIP, 1 mmol/l | S | 5.99 | 7.84 | 13.07 | 22.41 | 37.91 | 66.32 |
| | S/B | 4.4 | 6.6 | 14.4 | 18.7 | 66.5 | 236.9 |
| B. Luminol concentration = 0.48 mmol/liter | | | | | | | |
| Enhancer | B | 0.68 | 0.61 | 0.46 | 0.72 | 0.34 | 0.31 |
| PIP, 1 mmol/l | S | 5.0 | 6.53 | 10.96 | 19.2 | 30.09 | 47.03 |
| | S/SB | 7.4 | 10.7 | 23.8 | 26.7 | 88.5 | 151.7 |

EXAMPLE 13

Use of the Phenolic Enhancers 6-Bromonaphthol and 2,4-Dichlorophenol in Combination With an Organoboron Enhancer The procedure of Example 1 was followed except that the dilutions of the enhancer solutions were (A) K=1:20, 6-bromo-2-naphthol (6-BN)=1:5000

(B) K=1:10, 2,4-dichlorophenol (2,4-DCP)=1: 10, the HRP stock solution was diluted 1:500,000 and in experiment (B) only 5 µl of the dilute HRP solution was used. (The dilutions of enhancers were optimised).

The results in Table 15 show that even these less good phenolic enhancers are capable of giving a useful decrease in background and an increased (type II) signal:background ratio, when combined with an organoboron compound (4-biphenylboronic acid="K").

TABLE 15

| Enhancer(s) | B | S | S/B |
|---|---|---|---|
| A. 4-biphenylboronic acid (K) + 6-bromo-2-naphthol (6-BN) | | | |
| 1. K | 3562 | 178566 | 50.1 |
| 2. 6-BN | 5011 | 22811 | 4.6 |
| 1 + 2 (calculated) | 8573 | 201377 | 54.7 |
| 1 + 2 (observed) | 1915 | 172760 | 90.2 |
| B. 4-biphenylboronic acid (K) + 2,4-dichlorophenol (2,4-DCP) | | | |
| 1. K | 5346 | 700331 | 131.0 |
| 2. 2,4-DCP | 5178 | 44324 | 8.6 |
| 1 + 2 (calculated) | 10524 | 744655 | 139.6 |
| 1 + 2 (observed) | 2363 | 454329 | 192.3 |

We claim:

1. A method of enhancing a chemiluminescent reaction between a fused aromatic diacyl cyclic hydrazide (FADCH), a peroxidase enzyme and an oxidant, said enhancing increasing the signal to background ratio thereof, "signal" being light output in the presence of the peroxidase enzyme, "background" in its absence, which method comprises the step of carrying out said chemiluminescent reaction in the presence of an organoboron enhancer together with a nonboron-containing organic enhancer, said organoboron enhancer being selected from the group consisting of the compounds of formula (I)

in which the R groups are the same and each is selected from the group consisting of hydrogen, n-butyl, 4'-chlorophenyl and 3',5'-dicholorophenyl; or the R's together are 0,0-propylene thereby forming with the boron atom, a cyclic ether, W is selected from the group consisting of hydrogen, methyl, methoxy, hydroxy and chloro;

X is selected from the group consisting of hydrogen, chloro, amino and nitro;

Y is selected from the group consisting of hydrogen, methyl, carboxy, chloro, bromo, iodo, phenyl, phenoxy, 4'-chloroanilino, 4'-boronylphenyl, 4'-bromophenyl, 2'-carboxyethenyl and trimethylsilyl;

Z is selected from the group consisting of hydrogen, 5-chloro, 5-bromo, 5-(3'-trifluoromethyl)phenylazo and 6-chloro; or W and X together may represent a fused benzene ring and X and Y together may represent a fused benzene ring substituted by hydroxy in the 6-position of the naphthalene ring numbering, provided that (1) when each R is hydrogen;
  (a) W, X, Y, Z are each hydrogen; or
  (b) W, X and Z are each hydrogen and Y is selected from the group consisting of iodo, bromo, chloro, trimethylsilyl, phenoxy, phenyl, 4'-chloroanilino, methyl, 4'-boronylphenyl and 2'-carboxyethenyl; or
  (c) W and Z are each hydrogen and
    (i) X and Y together represent a fused benzene ring substituted by hydroxy in the 6-position of the naphthalene ring numbering: or
    (ii) X is either nitro or chloro and Y is chloro; or
    (iii) X is nitro and Y is carboxy;
  (d) W, Y and Z are each hydrogen and X is amino, chloro or nitro; or
  (e) W and X together represent a fused benzene ring and Y and Z are each hydrogen;
  (f) X and Y are each hydrogen:
    (i) W is methoxy and Z is 5-bromo; or
    (ii) W is hydroxy and Z is 5-(3'-trifluoromethyl)phenylazo; or
    (iii) W is methyl and Z is hydrogen;
  (g) W is chloro, X is chloro and Y and Z are each hydrogen; or
  (h) W and Y are each chloro, X is amino and Z is 6-chloro;
(2) when each R is n-butyl, W, X and Z are each hydrogen and Y is bromo or 4'-bromophenyl;
(3) when each R is 4'-chlorophenyl W, X and Z are each hydrogen and Y is chloro;
(4) when each R is 3',5'-dichlorophenyl W and Y are each hydrogen, X is chloro and Z is 5-chloro; and
(5) when the R's together represent 0,0-propylene, X, Y and Z are each hydrogen;

and the compounds bis(catechol)borate, boroglycine, pentaerythritol borate, 4-(3'-borono- 4'-hydroxy-phenylazo benzoic acid, diphenylisobutoxyborane, diphenylboronic anhydride and dimethylphenylboronic acids, said non-boron-containing organic enhancer being selected from the group consisting of phenolic enhancers and amine enhancers, said organoboron enhancer and said non-boron-containing enhancer being present in concentrations effective to increase the signal or signal to background ratio or to decrease the background, compared with carrying out said chemiluminescent reaction in the presence of each of said organoboron enhancer and said non-boron-containing organic enhancer alone.

2. A method according to claim 1 wherein the organoboron enhancer is selected from the group consisting of the compounds para-iodophenylboronic acid, para-bromophenylboronic acid, 4-biphenylboronic acid, 4-(trimethylsilyl)benzeneboronic acid, boroglycine, 2-hydroxy-5-[(3'-(trifluoromethyl)phenylazo]benzeneboronic acid, 4-chloro-3-nitrophenylboronic acid, 4-chlorophenylboronic acid, trans-4-(2'-carboxyethenyl) phenylboronic acid, 4-(4'-bromophenyl)phenyl-di-n-butoxyborane, 4-chlorophenyl-di-(4'-chlorophenoxy)borane, 4-4'-bis (phenylboronic acid), diphenylboronic anhydride, 4-(4'-chloroanilino)phenylboronic acid and 4-bromophenyl-di-n-butoxyborane.

3. A method according to claim 1 wherein the non boron-containing enhancer is any aromatic amine enhancer.

4. A method according to claim 43 wherein the organoboron enhancer is 4-biphenylboronic acid, 4-iodophenylboronic acid, trans-4-(2'-carboxyethenyl)phenylboronic acid or 4-bromophenylboronic acid and the phenolic enhancer is 4-iodophenol, 4-hydroxycinnamic, 4-imidazol-1-ylphenol, 4-phenylphenol or 4-bromophenol.

5. A method according to claim 1 wherein the enhancer is a phenolic enhancer selected from the group consisting of the compounds of formula (II)

wherein:
(i) A and Q are hydrogen; and
  $R_1$ is (a) halogen; (b) phenyl; (c)

$R_2$ being —CH$_2$—, —O— or —N=N— and V being hydrogen or $R_2$ being —O—, —S— or —S—S— and V being hydroxy;
(d)

(e)

(f) —CH=CH—$R_3$, $R_3$ being carboxy or 2,4-dinitrophenyl;
(g) —CH$_2$CH$_2$COOC$_2$H$_5$; or C$_1$-C$_6$ alkyl;

(j) imidazol-1-yl or benzimidazol-2-yl;
(k) 4-thiazolyl, 4-oxazolyl or 4-imidazolyl, each of which may be ring-substituted;
(l) 4-acetamido; and
(m) 1,2,3,4-thiatriazolyl-5-amino;
(ii) A is hydrogen;
Q is halogen or $C_{1-6}$ alkyl; and
$R_1$ is halogen;
(iii) A is halogen;
Q is hydrogen; and
$R_1$ is halogen or phenyl; or
(iv) A is hydrogen or halogen;
$R_1$ is —S(CH$_2$)$_n$—R$_4$ wherein n represents an integer of 1 to 5; $R_4$ represents hydrogen, cyano, morpholino, carboxylic acid, an alkoxycarbonyl group of 2 to 7 carbon atoms, metallic carboxylate, amido, aldehyde, or allyl, or is a phenyl group, which may be substituted by a halogen atom; or
$R_1$ and Q together represent a naphthalene nucleus-completing chain which, read in the direction from $R_1$ to Q, is of formula $R_5$ being hydrogen or halogen, whereby the compound of formula (II) is a beta-naphthol of formula (VI):

and "halogen" in every occurrence in (i), (ii), (iii) and (iv) above means chlorine, bromine or iodine.

6. A method according to claim 5 wherein the phenolic enhancer is selected from the group consisting of the compounds 4-chlorophenol, 4-bromophenol, 4-1iodophenol, 4-bromo-2-chlorophenol, 2,4-dichlorophenol, 3,4-dichlorophenol, 4-methylphenol, 4-tert-butylphenol, ethyl 3-(4-hydroxyphenyl) propionate, 4-benzylphenol, 4-(2',4'-dinitrostyryl)phenol, 4-hydroxycinnamic acid, 4-phenylphenol, 2-chloro-4-phenylphenol, 4-(4'-hydroxyphenyl)benzophenone, 4-(phenylazo)phenol, 4-(2' -carboxyphenylazo)phenol, 4-phenoxyphenol, 4-(4'-hydroxyphenoxy) phenol, 4-hydroxyphenyl sulphide, 4-hydroxyphenyl disulphide, (4-cyanomethylthio)phenol, 4-cyanomethylthio-2-fluorophenol, 4-cyanomethylthio-2-chlorophenol, 4-cyanomethylthio-2 -bromophenol, 4-imidazol-1-ylphenol, naphth-2-ol, 1-bromonaphth-2-ol, 6-bromonaphth-2-ol and 1,6-dibromonaphth-2-ol.

7. A method according to claim 1 wherein the peroxidase enzyme is free or conjugated to a ligand and the presence or amount of the peroxidase is determined from the presence or amount of light output of the chemiluminescent reaction.

8. A method according to claim 1 wherein the peroxidase is horseradish peroxidase.

9. A method according to claim 1 wherein the oxidant is hydrogen peroxide.

10. A method according to claim 1 wherein the FADCH is luminol.

11. A method according to claim 1 wherein the chemiluminescent reaction is carried out at a pH of from 7.5 to 9.

12. A method according to claim 1 wherein the organoboron enhancer is selected from the group consisting of the compounds of formula wherein:
(i) A and Q are hydrogen; and
$R_1$ is (a) halogen; (b) phenyl; (c)

$R_2$ being —CH$_2$—, —O— or —N=N— and V being hydrogen or $R_2$ being —O—, —S— or —S—S— and V being hydroxy;
(d)

(e)

(f) —CH=CH—R$_3$, R$_3$ being carboxy or 2,4-dinitrophenyl;
(g) —CH$_2$CH$_2$COOC$_2$H$_5$; or $C_1C_6$ alkyl;
(j) imidazol-1-yl or benzimidazol-2-yl;
(k) 4-thiazolyl, 4-oxazolyl or 4-imidazolyl, each of which may be ring-substituted;
(l) 4-acetamido; and
(m) 1,2,3,4-thiatriazolyl-5-amino;
(ii) A is hydrogen;
Q is halogen or $C_{1-6}$ alkyl; and
$R_1$ is halogen;
(ii) A is halogen;
Q is hydrogen; and
$R_1$ is halogen or phenyl; or
(iv) A is hydrogen or halogen;
$R_1$ is —S(CH$_2$)$_n$—R$_4$ wherein n represents an integer of 1 to 5; $R_4$ represents hydrogen, cyano, morpholino, carboxyl acid, an alkoxycarbonyl group of 2 to 7 carbon atoms, metallic carboxylate, amido, aldehyde, or allyl, or is a phenyl group, which may be substituted by a halogen atom; or
$R_1$ and Q together represent a naphthalene nucleus-completing chain which, read in the direction from $R_1$ to Q, is of formula

$R_5$ being hydrogen or halogen, whereby the compound of formula (II) is a beta-naphthol of formula (VI):

and "halogen" in every occurrence in (i), (ii), (iii) and (iv) above means chlorine, bromine or iodine.

13. A method according to claim 1 wherein the organoboron enhancer is 4-biphenylboronic acid, 4-iodophenylboronic acid, trans-4-(2'-carboxyethenyl))phenylboronic acid or 4-bromophenylboronic acid and the phenolic enhancer is 4-iodophenol, 4-hydroxycinnamic acid, 4-imidazol-1-ylphenol, 4-phenylphenol or 4-bromophenol.

14. A method of increasing the light, output or signal to background ratio of light output from a chemiluminescent reaction between a dihydrophthalazinedione (DPD), a peroxidase enzyme and an oxidant, "signal" being in the presence of the peroxidase enzyme, "background" in its absence, which method comprises the step of carrying out said chemiluminescent reaction in the presence of an organoboron enhancer together with a phenolic enhancer, said organoboron enhancer being selected from the group consisting of the compounds of formula (I)

in which the R groups are the same and each is selected from the group consisting of hydrogen, n-butyl, 4'-chlorophenyl and 3',5'-dichlorophenyl; or the R's together are 0,0-propylene thereby forming with the boron atom, a cyclic ether, W is selected from the group consisting of hydrogen, methyl, methoxy, hydroxy and chloro;

X is selected from the group consisting of hydrogen, chloro, amino and nitro;

Y is selected from the group consisting of hydrogen, methyl, carboxy, chloro, bromo, iodo, phenyl, phenoxy, 4'-chloroanilino, 4'-boronylphenyl, 4'-bromophenyl, 2'-carboxyethenyl and trimethylsilyl;

Z is selected from the group consisting of hydrogen, 5-chloro, 5-bromo, 5-(3'-trifluoromethyl)phenylazo and 6-chloro; or W and X together may represent a fused benzene ring and X and Y together may represent a fused benzene ring substituted by hydroxy in the 6-position of the naphthalene ring numbering, provided that

(1) when each R is hydrogen;
 (a) W, X, Y, Z are each hydrogen; or
 (b) W, X and Z are each hydrogen and Y is selected from the group consisting of iodo, bromo, chloro, trimethylsilyl, phenoxy, phenyl, 4'-chloroanilino, methyl, 4'-boronylphenyl and 2'-carboxyethenyl; or
 (c) W and Z are each hydrogen and
  (i) X and Y together represent a fused benzene ring substituted by hydroxy in the 6-position of the naphthalene ring numbering; or (ii) X is either nitro or chloro and Y is chloro; or
 (iii) X is nitro and Y is carboxy;
(d) W, Y and Z are each hydrogen and X is amino, chloro or nitro; or
(e) W and X together represent a fused benzene ring and Y and Z are each hydrogen;
(f) X and Y are each hydrogen:
 (i) W is methoxy and Z is 5-bromo; or
 (ii) W is hydroxy and Z is 5-(3'-trifluoromethyl)phenylazo; or
 (iii) W is methyl and Z is hydrogen;
(g) W is chloro, X is chloro and Y and Z are each hydrogen; or
(h) W and Y are each chloro, X is amino and Z is 6-chloro;
(2) when each R is n-butyl, W, X and Z are each hydrogen and Y is bromo or 4'-bromophenyl;
(3) when each R is 4'-chlorophenyl W, X and Z are each hydrogen and Y is chloro;
(4) when each R is 3',5'-dichlorophenyl W and Y are each hydrogen, X is chloro and Z is 5-chloro; and
(5) when the R's together represent 0,0-propylene, X, Y and Z are each hydrogen;

and the compounds bis(catechol)borate, boroglycine, pentaerythritol borate, 4-(3'-borono-4'-hydroxy-phenylazo benzoic acid, diphenylisobutoxyborane, diphenylboronic anhydride and dimethylphenylboronic acids.

15. A method of diagnostic assay of a substance, the presence or amount of which is relatable to the presence or amount of a reaction partner selected from the group consisting of a dihydrophthalazinedione (DPD), a peroxidase enzyme and an oxidant which together are reactable in a chemiluminescent reaction, which method comprises the steps of:

carrying out said chemiluminescent reaction in the presence of an organoboron enhancer together with a phenolic enhancer, said organoboron enhancer being selected from the group consisting of the compounds of formula (I)

in which the R groups are the same and each is selected from the group consisting of hydrogen, n-butyl, 4'-chlorophenyl and 3',5'-dichlorophenyl; or the R's together are 0,0-propylene thereby forming with the boron atom, a cyclic ether, W is selected from the group consisting of hydrogen, methyl, methoxy, hydroxy and chloro;

X is selected from the group consisting of hydrogen, chloro, amino and nitro;

Y is selected from the group consisting of hydrogen, methyl, carboxy, chloro, bromo, iodo, phenyl, phenoxy, 4'-chloroanilino, 4'-boronylphenyl, 4'-bromophenyl, 2'-carboxyethenyl and trimethylsilyl;

Z is selected from the group consisting of hydrogen, 5-chloro, 5-bromo, 5-(3'-trifluormethyl)phenylazo and 6-chloro; or W and X together may represent a fused benzene ring and X and Y together may represent a fused benzene ring substituted by hydroxy in the 6-position of the naphthalene ring numbering, provided that (1) when each R is hydrogen;

(a) W, X, Y, Z are each hydrogen; or
(b) W, X and Z are each hydrogen and Y is selected from the group consisting of iodo, bromo, chloro, trimethylsilyl, phenoxy, phenyl, 4'-chloroanilino, methyl, 4'-boronylphenyl and 2'-carboxyethenyl; or
(c) W and Z are each hydrogen and
  (i) X and Y together represent a fused benzene ring substituted by hydroxy in the 6-position of the naphthalene ring numbering; or
  (ii) X is either nitro or chloro and Y is chloro; or
  (iii) X is nitro and Y is carboxy;
(d) W, Y and Z are each hydrogen and X is amino, chloro or nitro; or
(e) W and X together represent a fused benzene ring and Y and Z are each hydrogen;.
(f) X and Y are each hydrogen:
  (i) W is methoxy and Z is 5-bromo; or
  (ii) W is hydroxy and Z is 5-(3'-trifluoromethyl)phenylazo; or
  (iii) W is methyl and Z is hydrogen;
(g) W is chloro, X is chloro and Y and Z are each hydrogen; or
(h) W and Y are each chloro, X is amino and Z is 6-chloro;
(2) when each R is n-butyl, W, X and Z are each hydrogen and Y is bromo or 4'-bromophenyl;
(3) when each R is 4'-chlorophenyl W, X and Z are each hydrogen and Y is chloro;
(4) when each R is 3',5'-dichlorophenyl W and Y are each hydrogen, X is chloro and Z is 5-chloro; and
(5) when the R's together represent O,O-propylene, X, Y and Z are each hydrogen;

and the compounds bis(catechol)borate, boroglycine, pentaerythritol borate, 4-(3'-borono- 4'-hydroxy-phenylazo benzoic acid, diphenylisobutoxyborane, diphenylboronic anhydride and dimethylphenylboronic acids, detecting or measuring the light output of the chemiluminescent reaction, and relating the presence or amount of the substance to be assayed to said light output.

16. A method according to claim 15 wherein the reaction partner is a peroxidase and the substance to be detected or measured an antigen or antibody.

17. A kit for use in a diagnostic assay, comprising in separate containers first and second enhancers which increase the signal or signal to background ratio of light output, in a chemiluminescent reaction of a fused aromatic diacyl cyclic hydrazide (FADCH), a peroxidase enzyme and an oxidant, "signal" being light output in the presence of the peroxidase enzyme, "background" in its absence, said first enhancer being an organoboron compound and the second enhancer a non-boron-containing organic compound selected from the group consisting of phenolic enhancers and amine enhancers, said organoboron compound being selected from the group consisting of the compounds of formula (I)

in which the R groups are the same and each is selected from the group consisting of hydrogen, n-butyl, 4'-chlorophenyl and 3',5'-dichlorophenyl; or the R's together are O,O-propylene thereby forming with the boron atom, a cyclic ether;

W is selected from the group consisting of hydrogen, methyl, methoxy, hydroxy and chloro;

X is selected from the group consisting of hydrogen, chloro, amino and nitro;

Y is selected from the group consisting of hydrogen, methyl, carboxy, chloro, bromo, iodo, phenyl, phenoxy, 4'-chloroanilino, 4'-boronylphenyl, 4'-bromophenyl, 2'-carboxyethenyl and trimethylsilyl;

Z is selected from the group consisting of hydrogen, 5-chloro, 5-bromo, 5-(3'-trifluormethyl)phenylazo and 6-chloro; or W and X together may represent a fused benzene ring and X and Y together may represent a fused benzene ring substituted by hydroxy in the 6-position of the naphthalene ring numbering, provided that
(1) when each R is hydrogen;
  (a) W, X, Y, Z are each hydrogen; or
  (b) W, X and Z are each hydrogen and Y is selected from the group consisting of iodo, bromo, chloro, trimethylsilyl, phenoxy, phenyl, 4'-chloroanilino, methyl, 4'-boronylphenyl and 2'-carboxyethenyl; or
  (c) W and Z are each hydrogen and
    (i) X and Y together represent a fused benzene ring substituted by hydroxy in the 6-position of the naphthalene ring numbering; or
    (ii) X is either nitro or chloro and Y is chloro; or
    (iii) X is nitro and Y is carboxy;
  (d) W, Y and Z are each hydrogen and X is amino, chloro or nitro; or
  (e) W and X together represent a fused benzene ring and Y and Z are each hydrogen;
  (f) X and Y are each hydrogen:
    (i) W is methoxy and Z is 5-bromo; or
    (ii) W is hydroxy and Z is 5-(3'-trifluoromethyl)phenylazo; or
    (iii) W is methyl and Z is hydrogen;
  (g) W is chloro, X is chloro and Y and Z are each hydrogen; or
  (h) W and Y are each chloro, X is amino and Z is 6-chloro;
(2) when each R is n-butyl, W, X and Z are each hydrogen and Y is bromo or 4'-bromophenyl;
(3) when each R is 4'-chlorophenyl W, X and Z are each hydrogen and Y is chloro;
(4) when each R is 3',5'-dichlorophenyl W and Y are each hydrogen, X is chloro and Z is 5-chloro; and
(5) when the R's together represent O,O-propylene, X, Y and Z are each hydrogen;

and the compounds bis(catechol)borate, boroglycine, pentaerythritol borate, 4-(3'-borono-4'-hydroxy-phenylazo benzoic acid, diphenylisobutoxyborane, diphenylboronic anhydride and dimethylphenylboronic acids.

18. A kit according to claim 17 which further comprises a FADCH.

19. A kit according to claim 18 wherein the FADCH is luminol and the kit further comprises a horseradish peroxidase.

20. A kit according to claim 17 which further comprises a peroxidase enzyme catalyst.

21. A kit according to claim 20 wherein the peroxidase is conjugated to a ligand.

22. A kit according to claim 21 the peroxidase is horseradish peroxidase.

23. A kit according to claim 17 wherein the organoboron enhancer is selected from the group consisting of the compounds para-iodophenylboronic acid, para-bromophenylboronic acid, 4-biphenylboronic acid, 4-(trimethylsilyl)benzeneboronic acid, boroglycine, 2-hydroxy-5-[(3'-(trifluoromethyl)phenylazo]benzeneboronic acid, 4-chloro-3-nitrophenylboronic acid, 4-chlorophenylboronic acid, trans-4-(2'-carboxyethenyl) phenylboronic acid, 4-(4'-bromophenyl)phenyl-di-n-butoxyborane, 4-chlorophenyl-di-(4'-chlorophenoxy)borane, 4-4'-bis (phenylboronic acid), diphenylboronic anhydride, 4-(4'-chloroanilino)phenylboronic acid and 4-bromophenyl-di- 2-butoxyborane.

24. A kit according to claim 17 wherein the non boron-containing enhancer is an aromatic amine enhancer.

25. A kit according to claim 17 wherein the non boron-containing enhancer is a phenolic enhancer is selected from the group consisting of the compounds of formula (II)

(II)

wherein:
(i) A and Q are hydrogen; and
$R_1$ is (a) halogen; (b) phenyl; (c)

(III)

$R_2$ being —$CH_2$—, —O— or —N=N— and V being hydrogen or $R_2$ being —O—, —S— or —S—S— and V being hydroxy;

(d)

(IV)

(e)

(V)

(f) —CH=CH—$R_3$, $R_3$ being carboxy or 2,4-dinitrophenyl;
(g) —$CH_2CH_2COOC_2H_5$; or $C_1$-$C_6$ alkyl;
(j) imidazol-1-yl or benzimidazol-2-yl;
(k) 4-thiazolyl, 4-oxazolyl or 4-imidazolyl, each of which may be ring-substituted;
(l) 4-acetamido; and
(m) 1,2,3,4-thiatriazolyl-5-amino;
(ii) A is hydrogen;
Q is halogen or $C_{1-6}$ alkyl; and
$R_1$ is halogen;
(iii) A is halogen;
Q is hydrogen; and
$R_1$ is halogen or phenyl; or
(iv) A is hydrogen or halogen;
$R_1$ is —$S(CH_2)_n$—$R_4$ wherein n represents an integer of 1 to 5; $R_4$ represents hydrogen, cyano, morpholino, carboxylic acid, an alkoxycarbonyl group of 2 to 7 carbon atoms, metallic carboxylate, amido, aldehyde, or allyl, or is a phenyl group, which may be substituted by a halogen atom; or $R_1$ and Q together represent a naphthalene nucleus-completing chain which, read in the direction from $R_1$ to Q, is of formula $$-\overset{5}{C}H=\overset{6}{C}-\overset{7}{C}H=\overset{8}{C}H-,$$
$$\phantom{-CH=}|\phantom{C-CH=CH-}$$
$$\phantom{-CH=}R_5$$

$R_5$ being hydrogen or halogen, whereby the compound of formula (II) is a beta-naphthol of formula (VI):

(VI)

and "halogen" in every occurrence in (i), (ii), (iii) and (iv) above means chlorine, bromine or iodine.

26. A kit according to claim 17 wherein the organoboron enhancer is selected from the group consisting of the compounds 4-chlorophenol, 4-bromophenol, 4-iodophenol, 4-bromo-2 -chlorophenol, 2,4-dichlorophenol, 3,4-dichlorophenol, 4-methylphenol, 4-tert-butylphenol, ethyl 3-(4-hydroxyphenyl) propionate, 4-benzylphenol, 4-(2',4'-dinitrostyryl)phenol, 4-hydroxycinnamic acid, 4-phenylphenol, 2-chloro-4-phenylphenol, 4-(4'-hydroxyphenyl)benzophenone, 4-(phenylazo)phenol, 4-(2' -carboxyphenylazo)phenol, 4-phenoxyphenol, 4-(4'-hydroxyphenoxy) phenol, 4-hydroxyphenyl sulphide, 4-hydroxyphenyl disulphide, (4-cyanomethylthio)phenol, 4-cyanomethylthio-2-fluorophenol, 4-cyanomethylthio-2-chlorophenol, 4-cyanomethylthio-2 -bromophenol, naphth-2-ol, 1-bromonaphth-2-ol, 6-bromonaphth-2-ol and 1,6-dibromonaphth-2-ol.

27. A Kit according to claim 17 wherein the organoboron enhancer is 4-biphenylboronic acid, 4-iodophenylboronic acid, trans-4-(2 '-carboxyethenyl)phenylboronic acid or 4-bromophenylboronic acid and the phenolic enhancer is 4-iodophenol, 4-hydroxycinnamic acid, 4-imidazol-1-ylphenol, 4-phenylphenol or 4-bromophenol.

28. A kit according to claim 17 which further comprises an oxidant.

29. A kit for use in a diagnostic assay, comprising in separate containers first and second enhancers which increase the signal or signal to background ratio of light output in a chemiluminescent reaction of a dihydrothalazinedione (DPD), a peroxidase enzyme and an oxidant, "signal" being light output in the presence of the peroxidase enzyme, "background" in its absence, the first enhancer being an organoboron compound and the second a phenolic enhancer, said organoboron compound being selected from the group consisting of the compounds of formula (I)

(I)

in which the R groups are the same and each is selected from the group consisting of hydrogen, n-butyl, 4'-chlorophenyl and 3',5'-dichlorophenyl; or the R's together are O,O-propylene thereby forming with the boron atom, a cyclic ether;

W is selected from the group consisting of hydrogen, methyl, methoxy, hydroxy and chloro;

X is selected from the group consisting of hydrogen, chloro, amino and nitro;

Y is selected from the group consisting of hydrogen, methyl, carboxy, chloro, bromo, iodo, phenyl, phenoxy, 4'-chloroanilino, 4'-boronylphenyl, 4'-bromophenyl, 2'-carboxyethenyl and trimethylsilyl;

Z is selected from the group consisting of hydrogen, 5-chloro, 5-bromo, 5-(3'-trifluoromethyl)phenylazo and 6-chloro; or W and X together may represent a fused benzene ring and X and Y together may represent a fused benzene ring substituted by hydroxy in the 6-position of the naphthalene ring numbering, provided that (1) when each R is hydrogen:
  (a) W, X, Y, Z are each hydrogen; or
  (b) W, X and Z are each hydrogen and Y is selected from the group consisting of iodo, bromo, chloro, trimethylsilyl, phenoxy, phenyl, 4'-chloroanilino, methyl, 4'-boronylphenyl and 2'-carboxyethenyl; or
  (c) W and Z are each hydrogen and
    (i) X and Y together represent a fused benzene ring substituted by hydroxy in the 6-position of the naphthalene ring numbering; or
    (ii) X is either nitro or chloro and Y is chloro; or
    (iii) X is nitro and Y is carboxy;
  (d) W, Y and Z are each hydrogen and X is amino, chloro or nitro; or
  (e) W and X together represent a fused benzene ring and Y and Z are each hydrogen;
  (f) X and Y are each hydrogen:
    (i) W is methoxy and Z is 5-bromo; or
    (ii) W is hydroxy and Z is 5-(3'-trifluoromethyl)phenylazo; or
    (iii) W is methyl and Z is hydrogen;
  (g) W is chloro, X is chloro and Y and Z are each hydrogen; or
  (h) W and Y are each chloro, X is amino and Z is 6-chloro;
(2) when each R is n-butyl, W, X and Z are each hydrogen and Y is bromo or 4'-bromophenyl;
(3) when each R is 4'-chlorophenyl W, X and Z are each hydrogen and Y is chloro;
(4) when each R is 3',5'-dichlorophenyl W and Y are each hydrogen, X is chloro and Z is 5-chloro; and
(5) when the R's together represent 0,0-propylene, X, Y and Z are each hydrogen;

and the compounds bis(catechol)borate, boroglycine, pentaerythritol borate, 4-(3'-borono-4'-hydroxy-phenylazo benzoic acid, diphenylisobutoxyborane, diphenylboronic anhydride and dimethylphenylboronic acids.

30. A kit according to claim 29 wherein the DPD is luminol.

* * * * *